(12) United States Patent
Goldring et al.

(10) Patent No.: US 10,323,982 B2
(45) Date of Patent: Jun. 18, 2019

(54) LOW-COST SPECTROMETRY SYSTEM FOR END-USER FOOD ANALYSIS

(71) Applicant: VERIFOOD, LTD., Herzliya (IL)

(72) Inventors: Damian Goldring, Tel Aviv (IL); Dror Sharon, Benei Atarot (IL)

(73) Assignee: VERIFOOD, LTD., Herzliya (IL)

( * ) Notice: Subject to any disclaimer, the term of this patent is extended or adjusted under 35 U.S.C. 154(b) by 0 days.

(21) Appl. No.: 15/411,922

(22) Filed: Jan. 20, 2017

(65) Prior Publication Data

US 2017/0254701 A1 Sep. 7, 2017
US 2018/0252580 A2 Sep. 6, 2018

Related U.S. Application Data

(63) Continuation of application No. 15/094,927, filed on Apr. 8, 2016, now Pat. No. 9,587,982, which is a
(Continued)

(51) Int. Cl.
*G01N 21/25* (2006.01)
*G01J 3/02* (2006.01)
(Continued)

(52) U.S. Cl.
CPC .......... *G01J 3/0256* (2013.01); *G01J 3/0208* (2013.01); *G01J 3/26* (2013.01); *G01J 3/2803* (2013.01);
(Continued)

(58) Field of Classification Search
CPC ........ G01J 3/02; G01J 3/26; G01J 3/28; G01J 3/42; G01J 3/51; G01J 9/00; G01N 21/25; G01N 21/33
See application file for complete search history.

(56) References Cited

U.S. PATENT DOCUMENTS 679,577 A 7/1901 Schaffner
5,469,252 A 11/1995 Doles et al.
(Continued)

FOREIGN PATENT DOCUMENTS

CN 1846114 A 10/2006
CN 101501465 A 8/2009
(Continued)

OTHER PUBLICATIONS

Acktar Advanced Coatings Website. Accessed Jun. 3, 2015. http://www.acktar.com/.
(Continued)

*Primary Examiner* — Abdullahi Nur
(74) *Attorney, Agent, or Firm* — Wilson Sonsini Goodrich & Rosati

(57) ABSTRACT

A compact spectrometer is disclosed that is suitable for use in mobile devices such as cellular telephones. In preferred embodiments, the spectrometer comprises a filter, at least one Fourier transform focusing element, a micro-lens array, and a detector, but does not use any dispersive elements. Methods for using the spectrometer as an end-user device for performing on-site determinations of food quality, in particular, by comparison with an updatable database accessible by all users of the device, are also disclosed.

18 Claims, 9 Drawing Sheets

Related U.S. Application Data continuation of application No. 14/356,144, filed as application No. PCT/IL2012/000367 on Oct. 31, 2012, now Pat. No. 9,377,396.

(60) Provisional application No. 61/555,043, filed on Nov. 3, 2011.

(51) Int. Cl.
 G01J 3/26 (2006.01)
 G01J 3/28 (2006.01)
 G01J 3/36 (2006.01)
 G01J 3/12 (2006.01)

(52) U.S. Cl.
 CPC .............. *G01J 3/36* (2013.01); *G01N 21/255* (2013.01); *G01J 2003/1226* (2013.01)

(56) References Cited

U.S. PATENT DOCUMENTS

| | | | |
|---|---|---|---|
| 5,966,212 A | 10/1999 | Hendler et al. | |
| 6,031,233 A | 2/2000 | Levin et al. | |
| 6,031,619 A | 2/2000 | Wilkens et al. | |
| 6,069,696 A | 5/2000 | McQueen et al. | |
| 6,072,576 A | 6/2000 | McDonald et al. | |
| 6,212,312 B1 | 4/2001 | Grann et al. | |
| 6,333,501 B1 | 12/2001 | Labrenz | |
| 6,441,375 B1 | 8/2002 | Joseph et al. | |
| 6,456,373 B1 | 9/2002 | Wienecke et al. | |
| 6,483,583 B1 | 11/2002 | Wright et al. | |
| 6,615,142 B1 | 9/2003 | Hovde | |
| 6,639,666 B2 | 10/2003 | Li | |
| 6,700,661 B1 | 3/2004 | Cadell et al. | |
| 6,717,669 B2 | 4/2004 | Ruiz | |
| 6,836,325 B2 | 12/2004 | Maczura et al. | |
| 6,864,978 B1 | 3/2005 | Hazen et al. | |
| 7,009,702 B2 | 3/2006 | Caruso et al. | |
| 7,038,774 B2 | 5/2006 | Hazen et al. | |
| 7,068,366 B2 | 6/2006 | Burk et al. | |
| 7,075,643 B2 | 7/2006 | Holub | |
| 7,084,974 B1 | 8/2006 | Barwicz et al. | |
| 7,145,650 B2 | 12/2006 | Wang et al. | |
| 7,151,600 B2 | 12/2006 | Imura | |
| 7,158,225 B2 | 1/2007 | Tedesco et al. | |
| 7,235,766 B2 | 6/2007 | Shur et al. | |
| 7,236,243 B2 | 6/2007 | Beecroft et al. | |
| 7,245,372 B2 | 7/2007 | Han | |
| 7,248,370 B2 | 7/2007 | Jones | |
| 7,251,037 B2 | 7/2007 | Jones | |
| 7,262,839 B2 | 8/2007 | Treado et al. | |
| 7,286,233 B2 | 10/2007 | Pizzi | |
| 7,339,665 B2 | 3/2008 | Imura | |
| 7,414,724 B2 | 8/2008 | Eckert et al. | |
| 7,420,663 B2 | 9/2008 | Wang et al. | |
| 7,426,446 B2 | 9/2008 | Hagler | |
| 7,433,042 B1 | 10/2008 | Cavanaugh et al. | |
| 7,436,511 B2 | 10/2008 | Ruchti et al. | |
| 7,489,396 B1 | 2/2009 | Vrhel et al. | |
| 7,528,957 B2 | 5/2009 | Lewis et al. | |
| 7,535,617 B2 | 5/2009 | Gupta et al. | |
| 7,649,627 B2 | 1/2010 | Yamamoto | |
| 7,667,740 B2 | 2/2010 | Hofer | |
| 7,697,136 B2 | 4/2010 | Imura | |
| 7,767,969 B2 | 8/2010 | Nagai et al. | |
| 7,805,319 B2 | 9/2010 | Badinelli | |
| 7,817,273 B2 | 10/2010 | Bahatt et al. | |
| 7,868,296 B2 | 1/2011 | Haran et al. | |
| 7,876,435 B2 | 1/2011 | Becker-Ross et al. | |
| 7,881,892 B2 | 2/2011 | Soyemi et al. | |
| 7,897,923 B2 | 3/2011 | Shelley et al. | |
| 7,907,282 B2 | 3/2011 | Coates | |
| 7,929,130 B2 | 4/2011 | Dirk | |
| 7,986,193 B2 | 7/2011 | Krah | |
| 7,999,933 B2 | 8/2011 | McClure | |
| 8,060,383 B2 | 11/2011 | Badinelli | |
| 8,125,633 B2 | 2/2012 | Whelan et al. | |
| 8,144,322 B2 | 3/2012 | Nagashima et al. | |
| 8,149,415 B2 | 4/2012 | Sanders et al. | |
| 8,169,607 B2 | 5/2012 | Sano et al. | |
| 8,169,608 B2 | 5/2012 | Sano et al. | |
| 8,247,774 B2 | 8/2012 | Chou et al. | |
| 8,269,174 B2 | 9/2012 | Gardner, Jr. et al. | |
| 8,274,739 B2 | 9/2012 | Lee et al. | |
| 8,284,401 B2 | 10/2012 | Choi et al. | |
| 8,330,945 B2 | 12/2012 | Choi et al. | |
| 8,462,420 B2 | 6/2013 | Lee et al. | |
| 8,477,305 B2 | 7/2013 | Shibayama et al. | |
| 8,526,002 B2 | 9/2013 | Deflores et al. | |
| 8,542,359 B2 | 9/2013 | Choi, II et al. | |
| 8,593,628 B2 | 11/2013 | Shimbo et al. | |
| 8,604,412 B2 | 12/2013 | Shibayama et al. | |
| 8,654,327 B2 | 2/2014 | Bohle et al. | |
| 8,665,440 B1 | 3/2014 | Kompaniets et al. | |
| 8,675,188 B2 | 3/2014 | Liu et al. | |
| 8,711,360 B2 | 4/2014 | Funamoto | |
| 8,711,362 B2 | 4/2014 | Funamoto | |
| 8,735,820 B2 | 5/2014 | Mertens | |
| 8,742,320 B2 | 6/2014 | Shibayama et al. | |
| 8,760,645 B2 | 6/2014 | Misener et al. | |
| 8,773,659 B2 | 7/2014 | McClure | |
| 8,786,854 B2 | 7/2014 | Miyazono | |
| 8,848,187 B2 | 9/2014 | Uematsu et al. | |
| 8,862,445 B2 | 10/2014 | Priore et al. | |
| 8,867,033 B2 | 10/2014 | Carron et al. | |
| 8,868,387 B2 | 10/2014 | Den Boef et al. | |
| 8,873,046 B2 | 10/2014 | Miyazono | |
| 8,937,717 B2 | 1/2015 | Preston et al. | |
| 8,976,357 B2 | 3/2015 | Uematsu et al. | |
| 9,030,662 B2 | 5/2015 | Lee et al. | |
| 9,060,113 B2 | 6/2015 | Rhoads et al. | |
| 9,063,011 B2 | 6/2015 | Chen et al. | |
| 9,074,933 B2 | 7/2015 | Yokino et al. | |
| 9,128,055 B2 | 9/2015 | Sekino et al. | |
| 9,163,986 B2 | 10/2015 | Bouckaert | |
| 9,173,508 B2 | 11/2015 | Tornwall et al. | |
| 9,182,280 B1 | 11/2015 | Gardner et al. | |
| 9,234,800 B2 | 1/2016 | Kawamata et al. | |
| 9,239,264 B1 | 1/2016 | Demers | |
| 9,291,504 B2 | 3/2016 | Goldring et al. | |
| 9,297,821 B2 | 3/2016 | Walter et al. | |
| 9,301,626 B2 | 4/2016 | Tornwall et al. | |
| 9,310,564 B2 | 4/2016 | Martinelli et al. | |
| 9,377,396 B2 | 6/2016 | Goldring et al. | |
| 9,383,258 B2 | 7/2016 | Goldring et al. | |
| 9,383,308 B2 | 7/2016 | Bradley et al. | |
| 9,395,244 B2 | 7/2016 | Kurokawa et al. | |
| 9,417,180 B2 | 8/2016 | Seo et al. | |
| 9,448,165 B2 | 9/2016 | Gulati et al. | |
| 9,453,794 B2 | 9/2016 | Gulati et al. | |
| 9,464,934 B2 | 10/2016 | Priore et al. | |
| 9,488,468 B2 | 11/2016 | Tsujii et al. | |
| 9,488,523 B2 | 11/2016 | Yokino et al. | |
| 9,508,765 B2 | 11/2016 | Owa et al. | |
| 9,518,917 B2 | 12/2016 | Scherer et al. | |
| 9,546,902 B2 | 1/2017 | Kovacich et al. | |
| 9,546,904 B2 | 1/2017 | Pawluczyk et al. | |
| 9,557,220 B2 | 1/2017 | Yasui et al. | |
| 9,568,363 B2 | 2/2017 | Yu et al. | |
| 9,587,982 B2 | 3/2017 | Goldring et al. | |
| 2001/0009972 A1 | 7/2001 | Doi et al. | |
| 2002/0039186 A1 | 4/2002 | Rosenberg et al. | |
| 2002/0131047 A1 | 9/2002 | Zarrabian et al. | |
| 2002/0163641 A1 | 11/2002 | Shroder | |
| 2002/0191127 A1 | 12/2002 | Roberts et al. | |
| 2004/0019462 A1* | 1/2004 | Gehrlein | B01F 3/02 702/188 |
| 2004/0136577 A1 | 7/2004 | Rao et al. | |
| 2004/0213459 A1 | 10/2004 | Ishimaru et al. | |
| 2005/0117151 A1 | 6/2005 | Han | |
| 2005/0128477 A1 | 6/2005 | Caruso et al. | |
| 2005/0149598 A1 | 7/2005 | Mendlovic et al. | |
| 2005/0151975 A1 | 7/2005 | Melnyk | |
| 2005/0196046 A1 | 9/2005 | Hudnut et al. | |

(56) References Cited

U.S. PATENT DOCUMENTS

| | | |
|---|---|---|
| 2006/0086901 A1 | 4/2006 | Price et al. |
| 2006/0124656 A1 | 6/2006 | Popovich, Jr. et al. |
| 2006/0132760 A1 | 6/2006 | Imura |
| 2006/0146315 A1 | 7/2006 | Treado |
| 2006/0279732 A1* | 12/2006 | Wang .................. G01J 3/02 356/326 |
| 2006/0280096 A1 | 12/2006 | Riley et al. |
| 2007/0230932 A1 | 10/2007 | Tanaka et al. |
| 2008/0061236 A1 | 3/2008 | Meredith et al. |
| 2008/0073510 A1 | 3/2008 | Finlay |
| 2008/0112853 A1* | 5/2008 | Hall .................. A61B 5/1495 422/82.05 |
| 2008/0137328 A1 | 6/2008 | Lee et al. |
| 2008/0204578 A1 | 8/2008 | Scheuch et al. |
| 2008/0265146 A1 | 10/2008 | Coates |
| 2008/0277625 A1 | 11/2008 | Nakamura et al. |
| 2008/0297791 A1 | 12/2008 | Imura |
| 2009/0051910 A1 | 2/2009 | Imura |
| 2009/0201577 A1 | 8/2009 | Laplante et al. |
| 2010/0080351 A1* | 4/2010 | Hession-Kunz ..... G01N 23/223 378/45 |
| 2010/0085537 A1 | 4/2010 | Ramella-Roman et al. |
| 2010/0110442 A1 | 5/2010 | Adibi et al. |
| 2010/0128370 A1 | 5/2010 | Chen et al. |
| 2010/0134794 A1 | 6/2010 | Odegard et al. |
| 2010/0165337 A1 | 7/2010 | Dirk |
| 2010/0191493 A1 | 7/2010 | Brown et al. |
| 2010/0201979 A1 | 8/2010 | Momtahan et al. |
| 2010/0245616 A1* | 9/2010 | Yoshino .............. A61B 1/0638 348/223.1 |
| 2010/0271352 A1 | 10/2010 | Nakano et al. |
| 2010/0284005 A1 | 11/2010 | Malinen et al. |
| 2010/0292581 A1 | 11/2010 | Howard et al. |
| 2010/0309454 A1 | 12/2010 | Zhang |
| 2011/0037975 A1 | 2/2011 | McClure |
| 2011/0255745 A1 | 10/2011 | Hodder et al. |
| 2011/0261252 A1 | 10/2011 | Chen |
| 2011/0318717 A1 | 12/2011 | Adamowicz |
| 2012/0018829 A1 | 1/2012 | Beck et al. |
| 2012/0019819 A1 | 1/2012 | Messerchmidt |
| 2012/0053426 A1 | 3/2012 | Webster et al. |
| 2012/0088486 A1 | 4/2012 | Messerchmidt |
| 2012/0286046 A1* | 11/2012 | Ciurczak ............. G01J 3/0262 235/454 |
| 2013/0021611 A1 | 1/2013 | Tsurutani |
| 2013/0107260 A1 | 5/2013 | Nozawa |
| 2013/0155402 A1 | 6/2013 | Walton et al. |
| 2013/0182250 A1 | 7/2013 | McClure |
| 2013/0258341 A1 | 10/2013 | Day et al. |
| 2014/0046630 A1 | 2/2014 | Smith et al. |
| 2014/0052555 A1 | 2/2014 | Macintosh |
| 2014/0168636 A1 | 6/2014 | Funamoto et al. |
| 2014/0293091 A1 | 10/2014 | Rhoads et al. |
| 2014/0333932 A1 | 11/2014 | Uematsu et al. |
| 2015/0036138 A1 | 2/2015 | Watson et al. |
| 2015/0055132 A1 | 2/2015 | Ricketts et al. |
| 2015/0062577 A1 | 3/2015 | Hartwell et al. |
| 2015/0103354 A1 | 4/2015 | Saptari et al. |
| 2015/0108333 A1 | 4/2015 | Bouckaert |
| 2015/0116707 A1 | 4/2015 | Tatsuda |
| 2015/0119661 A1 | 4/2015 | Gilbert et al. |
| 2015/0153225 A1 | 6/2015 | Baudelet |
| 2015/0204833 A1 | 7/2015 | O'Brien et al. |
| 2015/0292948 A1 | 10/2015 | Goldring et al. |
| 2015/0300879 A1 | 10/2015 | Goldring et al. |
| 2015/0323383 A1 | 11/2015 | Pastore et al. |
| 2016/0018260 A1 | 1/2016 | Samuels |
| 2016/0091369 A1 | 3/2016 | Sakurai et al. |
| 2016/0103069 A1 | 4/2016 | Umapathy et al. |
| 2016/0223400 A1 | 8/2016 | Carron et al. |
| 2016/0231171 A1 | 8/2016 | Assefa et al. |
| 2016/0245700 A1 | 8/2016 | Uematsu et al. |
| 2016/0258813 A1 | 9/2016 | Kuri |
| 2016/0263910 A1 | 9/2016 | Kanai et al. |
| 2016/0282182 A1 | 9/2016 | Kanai et al. |
| 2016/0299004 A1 | 10/2016 | Thamm |
| 2016/0305820 A1 | 10/2016 | Zollars et al. |
| 2016/0313184 A1 | 10/2016 | Owechko |
| 2016/0334274 A1 | 11/2016 | Xu |
| 2016/0356646 A1 | 12/2016 | Wiegand et al. |
| 2016/0356647 A1 | 12/2016 | Wiegand et al. |
| 2016/0356704 A1 | 12/2016 | Kim et al. |
| 2017/0003167 A1 | 1/2017 | Ave |
| 2017/0027447 A1 | 2/2017 | Sutin et al. |
| 2017/0038257 A1 | 2/2017 | Liu et al. |

FOREIGN PATENT DOCUMENTS

| | | |
|---|---|---|
| JP | H0792022 A | 4/1995 |
| JP | 2004294361 A | 10/2004 |
| JP | 2005148018 A | 6/2005 |
| JP | 2007218878 A | 8/2007 |
| JP | 2008286522 A | 11/2008 |
| JP | 2009104547 A | 5/2009 |
| JP | 2011198801 A | 10/2011 |
| WO | WO-9953350 A1 | 10/1999 |
| WO | WO-2010027982 A2 | 3/2010 |
| WO | WO-2013065035 A1 | 5/2013 |
| WO | WO-2013082272 A1 | 6/2013 |
| WO | WO-2013106307 A1 | 7/2013 |
| WO | WO-2013148461 A1 | 10/2013 |
| WO | WO-2013150290 A1 | 10/2013 |
| WO | WO-2013162850 A1 | 10/2013 |
| WO | WO-2013163268 A1 | 10/2013 |
| WO | WO-2013165887 A1 | 11/2013 |
| WO | WO-2014014534 A2 | 1/2014 |
| WO | WO-2014033783 A1 | 3/2014 |
| WO | WO-2014014534 A3 | 4/2014 |
| WO | WO-2014064447 A1 | 5/2014 |
| WO | WO-2014102629 A1 | 7/2014 |
| WO | WO-2014129305 A1 | 8/2014 |
| WO | WO-2014139003 A1 | 9/2014 |
| WO | WO-2014192007 A1 | 12/2014 |
| WO | WO-2015009602 A1 | 1/2015 |
| WO | WO-2015015493 A2 | 2/2015 |
| WO | WO-2015038372 A1 | 3/2015 |
| WO | WO-2015042617 A1 | 3/2015 |
| WO | WO-2015058166 A2 | 4/2015 |
| WO | WO-2015058166 A3 | 6/2015 |
| WO | WO-2015101992 A2 | 7/2015 |
| WO | WO-2015138028 A2 | 9/2015 |
| WO | WO-2015138028 A3 | 11/2015 |
| WO | WO-2016022283 A1 | 2/2016 |
| WO | WO-2016033224 A1 | 3/2016 |
| WO | WO-2016059946 A1 | 4/2016 |
| WO | WO-2016124659 A1 | 8/2016 |
| WO | WO-2016196727 A2 | 12/2016 |
| WO | WO-2016196727 A3 | 1/2017 |

OTHER PUBLICATIONS

Anoplate Website. Accessed Jun. 3, 2015. http://www.anoplate.com/capabilities/anoblack_ni.html.

Avian Technologies Website. Accessed Jun. 3, 2015. http://www.aviantechnologies.com/products/coatings/diffuse_black.php.

European search report and search opinion dated Jul. 24, 2015 for EP Application No. 12845773.6.

"Interference Filter Handbook," published by JDS Uniphase (Second Edition), Sep. 2006, p. 195-202 and 213-214.

International search report and written opinion dated Mar. 22, 2013 for PCT Application No. IL2012/000367.

Notice of allowance dated Mar. 29, 2016 for U.S. Appl. No. 14/356,144.

Notice of Allowance dated Oct. 26, 2016 for U.S. Appl. No. 15/094,927.

Office action dated Jul. 8, 2015 for U.S. Appl. No. 14/356,144.

Office action dated Jul. 8, 2016 for U.S. Appl. No. 15/094,927.

Office action dated Dec. 31, 2015 for U.S. Appl. No. 14/356,144.

\* cited by examiner

LOW-COST SPECTROMETRY SYSTEM FOR END-USER FOOD ANALYSIS

CROSS-REFERENCE

This application is a continuation of U.S. patent application Ser. No. 15/094,927, filed on Apr. 8, 2016, entitled "Low-Cost Spectrometry System for End-User Food Analysis", which is a continuation of U.S. patent application Ser. No. 14/356,144, filed on May 2, 2014, entitled "Low-Cost Spectrometry System for End-User Food Analysis", which is a national stage entry of PCT/IL2012/000367, filed on Oct. 31, 2012, entitled "Low-Cost Spectrometry System for End-User Food Analysis", which claims priority of U.S. Provisional Application Ser. No. 61/555,043, filed on Nov. 3, 2011, each of which is incorporated herein by reference in its entirety.

FIELD OF THE INVENTION

This invention relates to low-cost spectrometry systems. In particular, it relates to systems that do not use gratings but that have sufficient sensitivity and resolution to perform spectroscopic analysis, in particular via a distributed network, of substances (including complex mixtures), in particular foodstuffs, that are in the possession of the individual consumer.

BACKGROUND OF THE INVENTION

Food safety is a consumer issue of long standing. Even if a particular item was fresh at the time of its transportation to the point of sale or even at the time the end user obtains it, its freshness and safety at the actual time of use cannot be guaranteed. Thus, a method that would enable the end user to check a foodstuff for contamination immediately prior to consumption would be of major benefit to the consumer. Non-invasive methods, i.e. methods that do not involve removal or destruction of a portion of the food being tested, would be ideal, since such a method would provide ease of use and hence a higher likelihood of use.

Spectroscopic methods for determination of food safety meet the requirements of being non-invasive and of being easy in principle to use. There are two major obstacles that need to be overcome before use of such methods by the end user can become routine. The first is the necessity to provide an appropriate spectrometer. FIG. 1 shows a design of a typical spectrometer 10 known in the art. Light 105 enters through slit 100, is reflected from first mirror 101 onto a dispersive element such as a grating (103) which directs the light onto a second mirror 102. Because the light is dispersed by element 103 according to its wavelength, every pixel of the spectrometer's sensor 104 will be illuminated by a specific wavelength. Spectrometers that use this design are complicated, require precise alignment, are difficult to assemble and are limited in their miniaturization capabilities.

In contrast, a spectrometer suitable for routine consumer use must be small, rugged, easy to use, and capable of providing spectra of sufficient quality and resolution that meaningful conclusions about the content of the food being tested can be made. The second obstacle is that foods and their contaminants are in general not simple substances, but complex mixtures of substances that themselves tend to have complicated spectra. Thus, for such an end-user system to be useful, it must incorporate means for real-time analysis of the frequently complicated spectra obtained.

While development of such a spectrometry system would be a boon to end-user determination of food safety, its usefulness would extend far beyond such a limited use. For example, it could be used in applications as diverse as detection of environmental contaminants, remote detection of explosives or chemical or biological agents, or for remote diagnosis or monitoring of a patient's condition (e.g. blood oxygen or glucose levels).

There has thus been a considerable effort devoted to development of compact spectrometry systems to meet these needs. Some examples of compact spectrometry systems known in the art are given here.

U.S. Pat. No. 7,262,839 discloses a compact birefringent interference imaging spectrometer. This spectrometer comprises at least one liquid crystal cell or a micromechanical Fabry-Perot system that is used as a tunable filter. In some embodiments, the liquid crystal cell can be designed to create a series of bandpass zones. Different wavelengths are tuned across the x-y image field of a two-dimensional detector, enabling collection of wavelength resolved or spatially resolved spectral data.

U.S. Pat. No. 7,420,663 discloses a portable spectroscopic sensing device that is integrated into a mobile communication device such as a mobile telephone. The spectrometer uses the sensor associated with the camera located in the mobile communication device as a detector, and its connection with the mobile device allows uploading of the spectral information thus obtained to a remote location. The spectroscopic sensing device disclosed is based on a dispersive element such as a grating or prism, with all of the consequent drawbacks of such a device.

U.S. Pat. Appl. 2010/0201979 discloses a system and method for performing spectral-spatial mapping. Instead of a dispersive element such as a prism or grating, the system disclosed therein uses a cylindrical beam volume hologram (CVBH) to disperse the light. This design has the advantage that no slit or grating is needed, but suffers from drawbacks of low throughput and small spectral range. In addition, the expense of the CVBH element precludes its use in a spectrometer intended for consumers.

U.S. Pat. Appl. 2010/0309454 discloses a portable spectrometer integrated into a wireless communication device. Not only does the spectrometer disclosed therein depend on dispersive elements, but the system itself requires the use of a fiber optic cable attached to the wireless communication device to transmit light to the spectrometer, further limiting the ease of use and increasing the cost of the system.

Thus, a compact spectrometer system that can be integrated into a consumer device such as a cellular telephone while being sufficiently rugged and low in cost to be practical for end-user spectroscopic measurements of suspect items, and a convenient method by which the spectra obtained by such a spectrometer system (in particular those of complicated mixtures such as foodstuffs) can be analyzed and the likelihood of contamination estimated remains a long-felt yet unmet need.

SUMMARY OF THE INVENTION

The compact spectrometer system and method herein disclosed are designed to meet this long-felt need. A low-cost, rugged spectrometer with no dispersive elements or moving parts is disclosed, along with a method of using cloud computing via a continuously updatable database to analyze data obtained by the spectrometer and to return the results of the analysis to the user. The spectrometer system herein disclosed has a substantially straight optical axis and, in preferred embodiments, comprises no more than 2-4 elements excluding the detector. The alignment accuracy required between the elements is very low relative to that of spectrometers of the type illustrated in FIG. 1. The straight optical axis and small sensor size enable production of spectrometers that are small enough and economical enough to fit in devices such as cellular phones, and yet have sufficient sensitivity and resolution (typically <10 cm$^{-1}$) to obtain useful spectra of complex mixtures such as foodstuffs.

It is therefore an object of the present invention to disclose a compact spectrometer system for obtaining the spectrum of a sample, comprising (a) an optical detector for detecting light emanating from said sample; (b) an optical filter located between said sample and said detector; and (c) a first Fourier transform focusing element, wherein said compact spectrometer system does not contain any dispersive optical elements.

It is a further object of this invention to disclose such a compact spectrometer system, wherein said optical filter is a non-tunable filter.

It is a further object of this invention to disclose such a compact spectrometer system as defined in any of the above, wherein said first Fourier transform focusing element is disposed between said optical filter and said optical detector such that light passing through said optical filter is dispersed by said at least one focusing element onto the light-sensitive surface of said detector.

It is a further object of this invention to disclose such a compact spectrometer system as defined in any of the above, wherein the center wavelength of said optical filter varies with the incidence angle of light impinging thereupon.

It is a further object of this invention to disclose such a compact spectrometer system as defined in any of the above, wherein said optical filter comprises a plurality of sub-filters with different center wavelengths.

It is a further object of this invention to disclose such a compact spectrometer system, wherein said optical filter comprises a plurality of substantially parallel strips, each of which comprises a sub-filter.

It is a further object of this invention to disclose such a compact spectrometer system, wherein said optical filter comprises a plurality of substantially rectangular areas, each of which comprises a sub-filter.

It is a further object of this invention to disclose such a compact spectrometer system as defined in any of the above, wherein said optical filter is chosen from the group consisting of (a) Fabry-Perot filter, (b) thin-film filter, and (c) interference filter.

It is a further object of this invention to disclose such a compact spectrometer system as defined in any of the above, wherein said first Fourier transform focusing element is a plano-convex lens disposed such that its flat face faces said optical detector and its curved face faces said optical filter.

It is a further object of this invention to disclose such a compact spectrometer system as defined in any of the above, further comprising a second Fourier transform focusing element.

It is a further object of this invention to disclose such a compact spectrometer system, wherein said Fourier transform focusing elements are plano-convex cylindrical lenses disposed such that the flat face of each lens faces said optical detector, the curved face of each lens faces said optical filter, the focal lines of the two lenses are oriented along different axes in the x-y plane, and the focal planes of said Fourier transforming focusing elements substantially coincide.

It is a further object of this invention to disclose such a compact spectrometer system, wherein the focal planes of said Fourier transforming focusing elements are substantially coincident with light-sensitive surface of said optical detector.

It is a further object of this invention to disclose such a compact spectrometer system, wherein the focal lines of said Fourier transform focusing elements are perpendicular.

It is a further object of this invention to disclose such a compact spectrometer system as defined in any of the above, further comprising a micro-lens array.

It is a further object of this invention to disclose such a compact spectrometer system, wherein said micro-lens array is located in the focal plane of said first Fourier transform focusing element.

It is a further object of this invention to disclose such a compact spectrometer system, wherein said detector is located at a plane substantially perpendicular to the optical axis such that the micro-lenses form multiple images of said optical filter on said optical detector.

It is a further object of this invention to disclose such a compact spectrometer system, wherein said optical filter comprises a plurality of sub-filters with different center wavelengths.

It is a further object of this invention to disclose such a compact spectrometer system, further comprising a second Fourier transforming focusing element, wherein said micro-lens array comprises an array of cylindrical lenses and is located at the focal plane of first of two said focusing elements and said optical detector is located at the focal plane of second of two said focusing elements.

It is a further object of this invention to disclose such a compact spectrometer system as defined in any of the above, further comprising a diffuser disposed between said sample and said optical filter.

It is a further object of this invention to disclose such a compact spectrometer system as defined in any of the above, wherein said first Fourier transform focusing element is a lens chosen from the group consisting of (a) plano-convex lenses, (b) biconvex lenses, and (c) aspheric lenses, and further wherein said optical filter is located between said first Fourier transform focusing element and said sample.

It is a further object of this invention to disclose such a compact spectrometer system, wherein said optical filter comprises a plurality of sub-filters with different center wavelengths.

It is a further object of this invention to disclose such a compact spectrometer system, wherein said plurality of sub-filters is disposed radially about a center point.

It is a further object of this invention to disclose such a compact spectrometer system, wherein said optical filter is in close proximity to said optical detector.

It is a further object of this invention to disclose such a compact spectrometer system as defined in any of the above, wherein said optical detector is a two-dimensional image sensor.

It is a further object of this invention to disclose such a compact spectrometer system as defined in any of the above, further comprising a light source adapted to illuminate said sample.

It is a further object of this invention to disclose such a compact spectrometer system, wherein said light source is a laser.

It is a further object of this invention to disclose such a compact spectrometer system, wherein said light source is a light-emitting diode.

It is a further object of this invention to disclose such a compact spectrometer system, further comprising a focusing system adapted focus light from said light source at a predetermined location relative to said sample.

It is a further object of this invention to disclose such a compact spectrometer system, wherein said focusing system is an autofocus system.

It is a further object of this invention to disclose such a compact spectrometer system, wherein said focusing system controls the position of a lens that focuses light produced by said light source onto said sample.

It is a further object of this invention to disclose such a compact spectrometer system, wherein said focusing system controls the optical properties of a lens that focuses light produced by said light source onto said sample.

It is a further object of this invention to disclose such a compact spectrometer system, wherein said focusing system comprises a voice-coil motor.

It is a further object of this invention to disclose such a compact spectrometer system, wherein said focusing system comprises a piezoelectric motor.

It is a further object of this invention to disclose such a compact spectrometer system, wherein said focusing system comprises a micro-electrical-mechanical-system (MEMS) motor.

It is a further object of this invention to disclose such a compact spectrometer system as defined in any of the above, wherein said light emanating from said sample comprises light scattered by said sample upon illumination.

It is a further object of this invention to disclose such a compact spectrometer system, wherein said spectrum is selected from the group consisting of (a) molecular vibrational spectra, (b) molecular rotational spectra, and (c) electronic spectra. In some preferred embodiments of said compact spectrometer system, the spectrum is a Raman spectrum.

It is a further object of this invention to disclose such a compact spectrometer system, further comprising a second optical filter.

It is a further object of this invention to disclose such a compact spectrometer system, wherein said light scattered from said sample upon illumination comprises light reflected by said sample upon illumination.

It is a further object of this invention to disclose such a compact spectrometer system as defined in any of the above, wherein said light emanating from said sample comprises light produced by fluorescence emanating from said sample.

It is a further object of this invention to disclose such a compact spectrometer system as defined in any of the above, further comprising means for communicating with a communication network.

It is a further object of this invention to disclose such a compact spectrometer system, wherein said communication network is a wireless communication network.

It is a further object of this invention to disclose such a compact spectrometer system, wherein said compact spectrometer system is enclosed within a mobile communication device associated with said communication network.

It is a further object of this invention to disclose such a compact spectrometer system, wherein said mobile communication device is a cellular telephone.

It is a further object of this invention to disclose such a compact spectrometer system, further comprising a database of spectral information in communication with said communication network.

It is a further object of this invention to disclose such a compact spectrometer system, wherein said database is continuously updatable in real time.

It is a further object of this invention to disclose such a compact spectrometer system as defined in any of the above, further comprising a local digital processor.

It is a further object of this invention to disclose such a compact spectrometer system, wherein said local digital processor is programmed to perform at least one algorithm chosen from the group consisting of (a) an algorithm for operating said compact spectrometer system; (b) an algorithm for processing raw spectral data obtained by said compact spectrometer system; (c) an algorithm for comparing data obtained by said compact spectrometer system with data stored in a database; and (c) an algorithm for transmitting spectral data obtained by said compact spectrometer system to a remote server.

It is a further object of this invention to disclose such a compact spectrometer system as defined in any of the above, further comprising local memory.

It is a further object of this invention to disclose such a compact spectrometer system, wherein said local memory is chosen from the group consisting of (a) fixed memory and (b) volatile memory.

It is a further object of this invention to disclose such a compact spectrometer system, further comprising a local database of spectral information stored within said local memory.

It is a further object of this invention to disclose such a compact spectrometer system as defined in any of the above, wherein said compact spectrometer system is incorporated into an oven.

It is a further object of this invention to disclose such a compact spectrometer system, wherein said oven is a microwave oven.

It is a further object of this invention to disclose such a compact spectrometer system as defined in any of the above, wherein said compact spectrometer system is incorporated into a refrigerator.

It is a further object of this invention to disclose such a compact spectrometer system as defined in any of the above, further comprising GPS positioning means for determining the location of said spectrometer system.

It is a further object of this invention to disclose such a compact spectrometer system as defined in any of the above, wherein said sample comprises food.

It is a further object of this invention to disclose a method of obtaining a spectrum of a sample without using dispersive optics, wherein said method comprises: providing a sample; causing light emanating from said sample to impinge on an optical filter, the center wavelength of which depends on the angle of incidence of the light impinging upon it; passing said light to a first Fourier transform focusing element; measuring the intensity of light as a function of position in a predetermined plane $P_1$; and converting the intensity of light as a function of position in said plane $P_1$ to a spectrum.

It is a further object of this invention to disclose such a method, wherein said step of measuring the intensity of light as a function of position in a predetermined plane $P_1$ comprises measuring the intensity of light as a function of position in a plane substantially coincident with the focal plane of said first Fourier transform focusing element.

It is a further object of this invention to disclose such a method as defined in any of the above, wherein said step of causing light emanating from said sample to impinge on an optical filter precedes said step of passing said light to a first Fourier transform focusing element, whereby the light passing through said optical filter is angle-encoded according to its wavelength and said light is transformed by said Fourier transform focusing element to spatially encoded.

It is a further object of this invention to disclose such a method as defined in any of the above, wherein said step of passing said light to a first Fourier transform focusing element precedes said step of causing light emanating from said sample to impinge on an optical filter.

It is a further object of this invention to disclose such a method as defined in any of the above, further comprising a step of placing in said predetermined plane $P_1$ an image sensor adapted to measure the intensity of light impinging upon said image sensor as a function of position.

It is a further object of this invention to disclose such a method as defined in any of the above, wherein said step of passing said light to a first Fourier transform focusing element comprises a step of passing said light to a plano-convex lens, the curved surface of which is facing said optical filter.

It is a further object of this invention to disclose such a method as defined in any of the above, wherein said step of causing light emanating from said sample to impinge on an optical filter comprises a step of causing light emanating from said sample to impinge on an optical filter comprising a plurality of sub-filters.

It is a further object of this invention to disclose such a method, further comprising placing a micro-lens array in a predetermined plane $P_2$ oriented such that each micro-lens samples the optical Fourier transform formed at said plane $P_2$, thereby creating a micro-image of the aperture of said optical filter at a predetermined plane $P_3$, and thereby decomposing the sampling points of said optical Fourier transform according to the origin of the light at a particular sub-filter reaching said micro-lens.

It is a further object of this invention to disclose such a method, wherein said predetermined plane $P_2$ is substantially identical to the focal plane of said first Fourier transform focusing element.

It is a further object of this invention to disclose such a method, further comprising a step of placing an image sensor adapted to measure the intensity of light impinging upon said image sensor as a function of position in said predetermined plane $P_3$.

It is a further object of this invention to disclose such a method, further comprising placing said plurality of sub-filters along a single axis and passing said angle-encoded light through a second Fourier transform focusing element disposed such that the spatially encoded light produced by said second Fourier transform focusing element is encoded at an angle relative to the orientation of the spatially encoded light produced by said first Fourier transform focusing element and such that the focal plane of said second Fourier transform focusing element is substantially identical with said predetermined plane $P_3$; wherein said step placing a micro-lens array between said first Fourier transform focusing element and said predetermined plane $P_3$ further comprises placing a micro-lens array comprising cylindrical micro-lenses disposed such that the light passing through said micro-lens array is disposed in said plane along an axis parallel to said single axis.

It is a further object of this invention to disclose such a method, wherein said step of passing said angle-encoded light to a first Fourier transform focusing element comprises a step of passing said angle-encoded light to a first plano-convex cylindrical lens, the curved surface of which is facing said optical filter, and said step of passing said angle-encoded light through a second Fourier transform focusing element comprises a step of passing said angle-encoded light to a second plano-convex cylindrical lens, the curved surface of which is facing said optical filter.

It is a further object of this invention to disclose such a method, further comprising placing said micro-lens array in the focal plane of said first Fourier transform focusing element; and placing said optical detector in the focal plane of said second Fourier transform focusing element.

It is a further object of this invention to disclose such a method as defined in any of the above, further comprising passing said light through a diffuser.

It is a further object of this invention to disclose such a method as defined in any of the above, further comprising illuminating said sample with a light source.

It is a further object of this invention to disclose such a method, wherein said step of illuminating said sample comprises illuminating said sample with a light source chosen from the group consisting of lasers and light emitting diodes.

It is a further object of this invention to disclose such a method as defined in any of the above, wherein said spectrum is selected from the group consisting of (a) molecular vibrational spectra, (b) molecular rotational spectra, and (c) electronic spectra. In some preferred embodiments of said method, the spectrum is a fluorescence spectrum. In some preferred embodiments of said method, the spectrum is a Raman spectrum.

It is a further object of this invention to disclose such a method as defined in any of the above, wherein said spectrum is a fluorescence spectrum.

It is a further object of this invention to disclose such a method, further comprising a step of separating the Raman signal from the fluorescence signal.

It is a further object of this invention to disclose such a method, further comprising a step of focusing light emanating from said light source to a predetermined location relative to said sample.

It is a further object of this invention to disclose such a method, wherein said step of focusing light emanating from said light source comprises a step of focusing light emanating from said light source using an autofocus system.

It is a further object of this invention to disclose such a method, wherein said step of focusing light emanating from said light source using an autofocus system further comprises analyzing in real time the signal obtained by said spectrometer; and commanding said autofocus system accordingly, so that said light is focused to the optimal signal extraction point at the sample.

It is a further object of this invention to disclose such a method as defined in any of the above, further comprising analyzing the spectrum obtained by comparison with a database of spectral information.

It is a further object of this invention to disclose such a method, wherein said step of analyzing comprises at least one step chosen from (a) comparing said spectrum with spectra in a spectral database; (b) comparing said spectrum with spectra in a spectral database by using Principal Components Analysis; (c) comparing said spectrum with spectra in a spectral database by using Partial Least Squares analysis; and (d) comparing said spectrum with spectra in a spectra database by using a neural network algorithm.

It is a further object of this invention to disclose such a method, further comprising adding said spectrum to said spectral database.

It is a further object of this invention to disclose such a method, further comprising transmitting said spectrum to a remote processing unit; using said remote processing unit to perform said step of analyzing; and transmitting the results of said step of analyzing to the user.

It is a further object of this invention to disclose such a method, wherein said steps of transmitting are performed by transmitting over a wireless network.

It is a further object of this invention to disclose such a method, further comprising performing a preliminary analysis of said spectrum obtained in said step of converting the intensity of light as a function of position in the focal plane of said first Fourier transform focusing element.

It is a further object of this invention to disclose such a method, wherein said step of performing a preliminary analysis of said spectrum is performed using a local processing unit.

It is a further object of this invention to disclose such a method, wherein said step of performing a preliminary analysis of said spectrum is performed remotely.

It is a further object of this invention to disclose such a method, wherein said step of performing a preliminary analysis of said spectrum further comprises at least one step chosen from the group consisting of (a) averaging a plurality of independent measurements; (b) compensating for optical aberrations; and (c) reducing detector noise using a noise reduction algorithm.

It is a further object of this invention to disclose such a method as defined in any of the above, further comprising a step of transmitting to a predetermined remote location the location at which said spectrum is obtained.

It is a further object of this invention to disclose such a method as defined in any of the above, said step of transmitting to a predetermined remote location the location at which said spectrum is obtained further comprises a step of determining the location at which said spectrum by use of a GPS.

It is a further object of this invention to disclose such a method as defined in any of the above, wherein said steps of causing light emanating from said sample to impinge on an optical filter, the center wavelength of which depends on the angle of incidence of the light impinging upon it; passing said light to a first Fourier transform focusing element; and measuring the intensity of light as a function of position in said plane $P_1$ are performed by using optical elements, all of which are disposed within or upon a mobile communication device.

It is a further object of this invention to disclose such a method, wherein said mobile communication device is a cellular telephone.

It is a further object of this invention to disclose such a method as defined in any of the above, wherein said steps of causing light emanating from said sample to impinge on an optical filter, the center wavelength of which depends on the angle of incidence of the light impinging upon it; passing said light to a first Fourier transform focusing element; and measuring the intensity of light as a function of position in said plane $P_1$ are performed by using optical elements, all of which are disposed within or upon an oven.

It is a further object of this invention to disclose such a method, wherein said oven is a microwave oven.

It is a further object of this invention to disclose such a method as defined in any of the above, wherein said steps of causing light emanating from said sample to impinge on an optical filter, the center wavelength of which depends on the angle of incidence of the light impinging upon it; passing said light to a first Fourier transform focusing element; and measuring the intensity of light as a function of position in said plane $P_1$ are performed by using optical elements, all of which are disposed within or upon a refrigerator.

It is a further object of this invention to disclose such a method as defined in any of the above, wherein said sample comprises food.

It is a further object of this invention to disclose such a method as defined in any of the above, wherein said sample comprises medication.

BRIEF DESCRIPTION OF THE DRAWINGS

The invention will now be described with reference to the drawings, wherein.

DETAILED DESCRIPTION OF THE PREFERRED EMBODIMENTS

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

As used herein, the term "dispersive" is used, with respect to optical components, to describe a component that is designed to direct light in space according to its wavelength, and thus to separate spatially the different wavelength components of a polychromatic beam of light. Non-limiting examples of "dispersive" optical elements by this definition include diffraction gratings and prisms. The term specifically excludes elements such as lenses that disperse light because of non-idealities such as chromatic aberration or elements such as interference filters that have different transmission profiles according to the angle of incident radiation.

Figure 1:
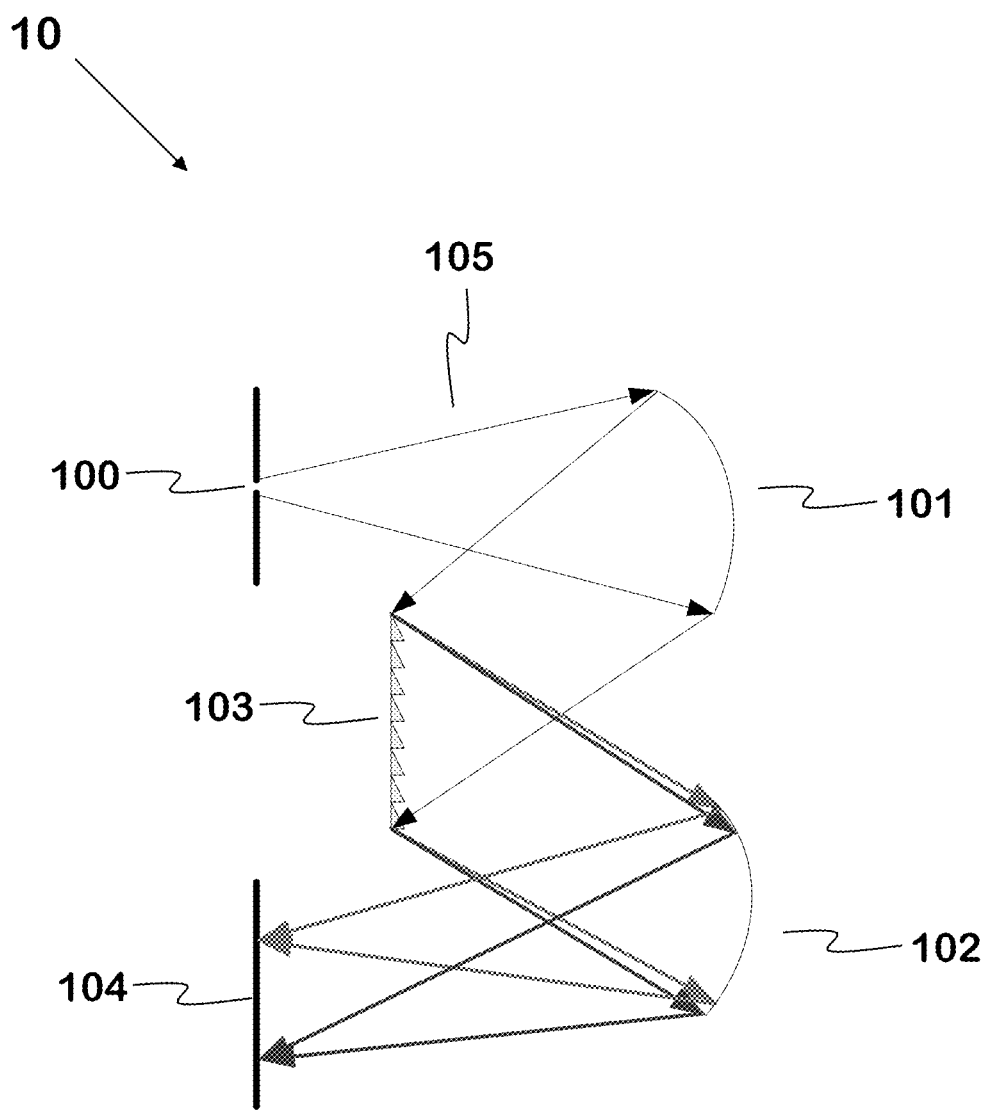
FIG. 1 presents a schematic diagram of a grating-based spectrometer according known in the art.
Figure 2A:
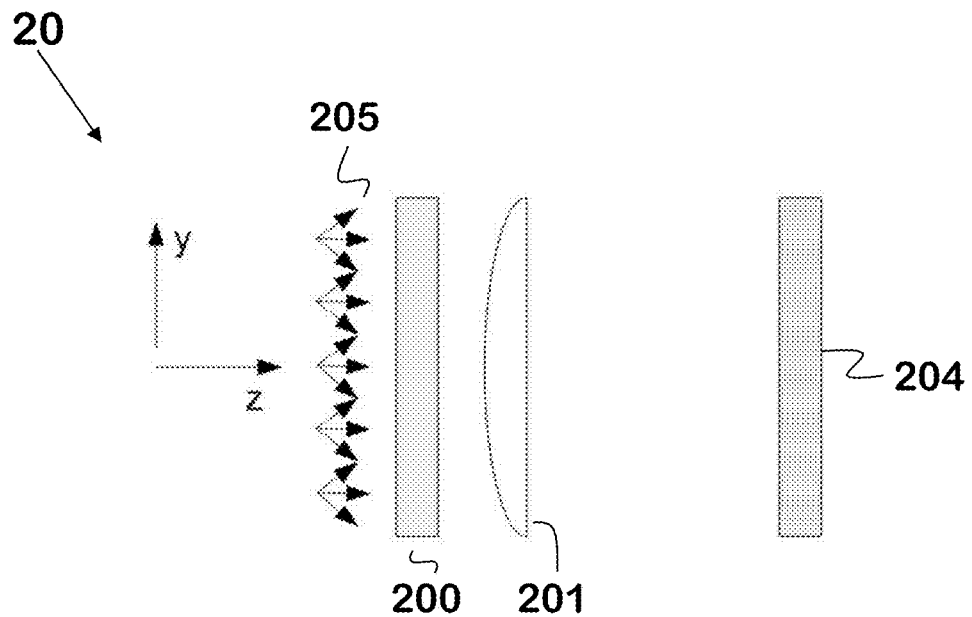
FIGS. 2A-2E present schematic diagrams of the optical layouts of several non-limiting embodiments of the compact spectrometer system herein disclosed.

Reference is now made to FIG. 2A, which illustrates one non-limiting embodiment of the compact spectrometer system 20 herein disclosed. The system comprises an optical filter 200, a first Fourier transform focusing element 201, and a detector 204. In preferred embodiments of the invention, the first Fourier transform focusing element 201 is a plano-convex lens oriented such that the convex side is facing the optical filter. The detector is located in a predetermined plane $P_1$, which in preferred embodiments of the invention is the focal plane of the first Fourier transform focusing element.

Optical filter 200 can be of any type known in the art. Non-limiting examples of suitable optical filters include Fabry-Perot (FP) resonators, cascaded FP resonators, and interference filters. In a typical embodiment of the simplest possible arrangement shown in FIG. 2A, a narrow bandpass filter ($<10$ cm$^{-1}$) with a wide blocking range outside of the transmission band (at least 200 nm) can be used. In preferred embodiments, the center wavelength (CWL) of the filter varies with the incident angle of the light impinging upon it.

Detector 204 may be of any suitable type known in the art capable of detecting light in the wavelength range of interest; the compact spectrometer system disclosed herein can be used from the UV to the IR, depending on the nature of the spectrum being obtained and the particular spectral properties of the sample being tested. Because, as will be explained below, spectra are obtained by measuring the intensity of light as a function of the position in a predetermined plane (e.g. the focal plane of the first Fourier transform focusing element), in preferred embodiments of the invention, a detector that is capable of measuring intensity as a function of position (e.g. an array detector or a two-dimensional image sensor) is used.

The basic principle of operation of compact spectrometer 20 is as follows. Light 205 impinges upon optical filter 200. Assuming that light 205 is approximately spatially invariant over the area of the optical filter (in typical embodiments of the invention, the entrance aperture has an area of the order of 1 mm$^2$), and that the light impinges upon the filter at a sufficiently wide range of propagation angles, both of which are reasonable assumptions, the light passing through the filter is angularly encoded after passing through the optical filter. The first Fourier transform focusing element (201) performs (approximately) a spatial Fourier transform of the angle-encoded light, transforming it into a spatially-encoded spectrum. That is, the intensity of light recorded by the sensor as a function of position (pixel number) on the sensor is correlated to the intensity at wavelength of the light corresponding to that position.

Figure 3:
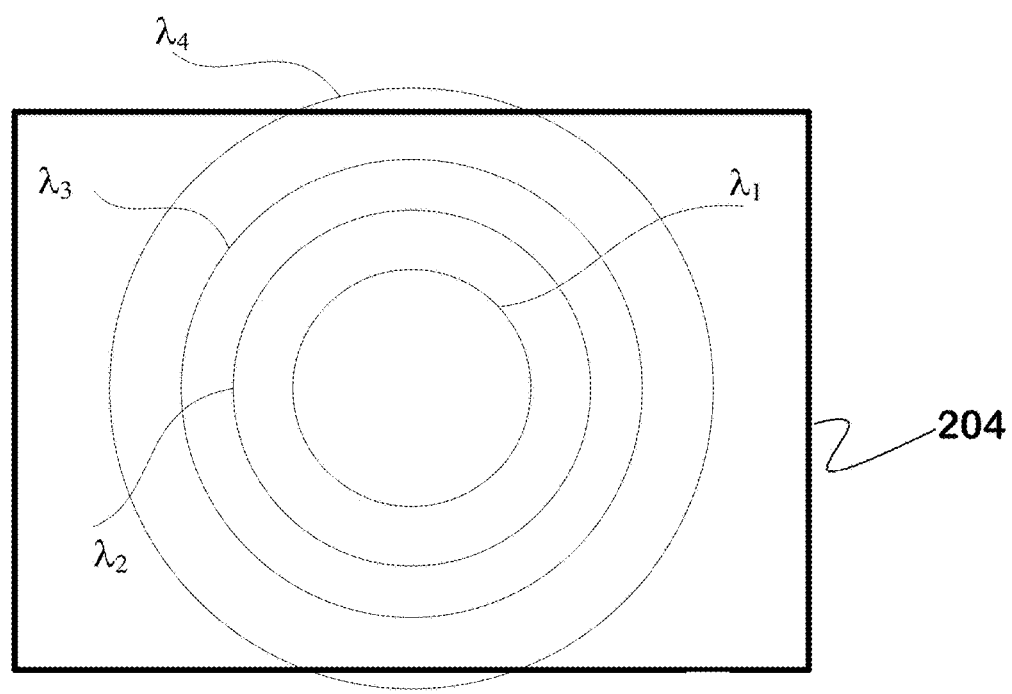
FIG. 3 presents a schematic illustration of the dispersion of light upon a detector according to one embodiment of the compact spectrometer system herein disclosed.

Reference is now made to FIG. 3, which illustrates the dispersion of light on detector 204 for an embodiment in which the detector is a 2-D image sensor located in plane $P_1$ which is substantially coincident with the focal plane of first Fourier transform focusing element 201, and the first Fourier transform focusing element is a lens with radial symmetry. As can be seen in the figure, light of different wavelengths ($\lambda_1, \lambda_2, \lambda_3, \lambda_4$, etc.) will arrive at the detector as a series of circles of different radii proportional to the wavelength. In general, the relationship between the wavelength and the radius of the corresponding circle will not be linear.

Figure 2B:
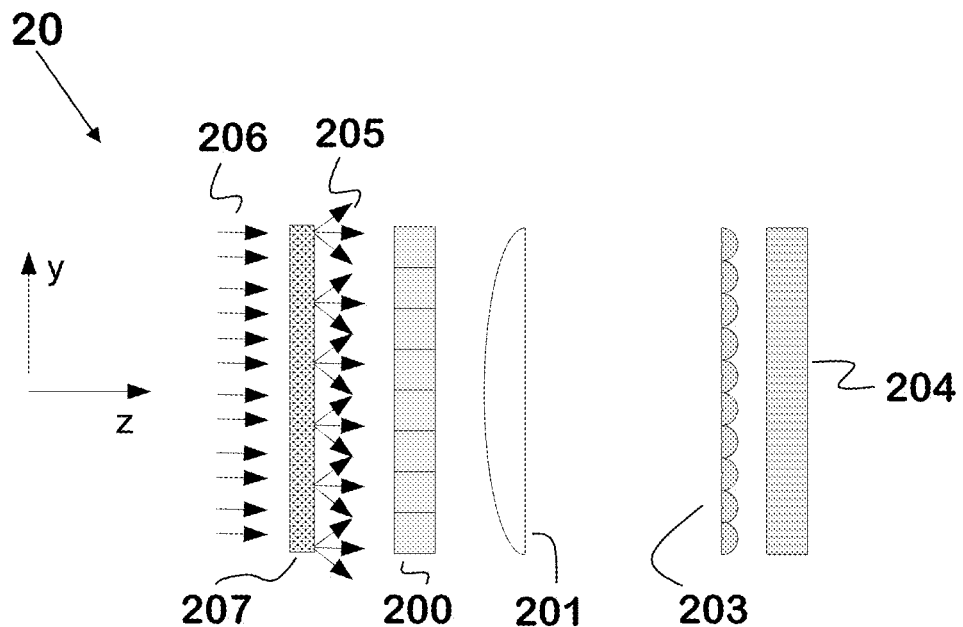

In embodiments in which the light emanating from the sample is not sufficiently diffuse, a diffuser is placed in front of the optical filter. Reference is now made to FIG. 2B, which illustrates a typical embodiment of compact spectrometer system 20 that incorporates a diffuser. Collimated (or partially collimated light) 206 impinges on the diffuser, which then produces diffuse light 205 which then impinges on optical filter 200.

The use of a single filter, as shown in FIG. 2A, can limit the spectral range available to the spectrometer. For example, if the angle of incidence of light is larger than 30°, the system will probably not produce a signal of sufficient intensity due to lens aberrations and the decrease in the efficiency of the detector at large angles. For an angular range of 30° and an optical filter CWL of ~850 nm, the spectral range available to the spectrometer will be ~35 nm. This range is insufficient for many applications such as Raman spectroscopy. In embodiments with larger spectral ranges, an optical filter that is actually composed of a plurality of sub-filters, in which each sub-filter has a different CWL and thus covers a different part of the optical spectrum, is used.

Figure 4A:
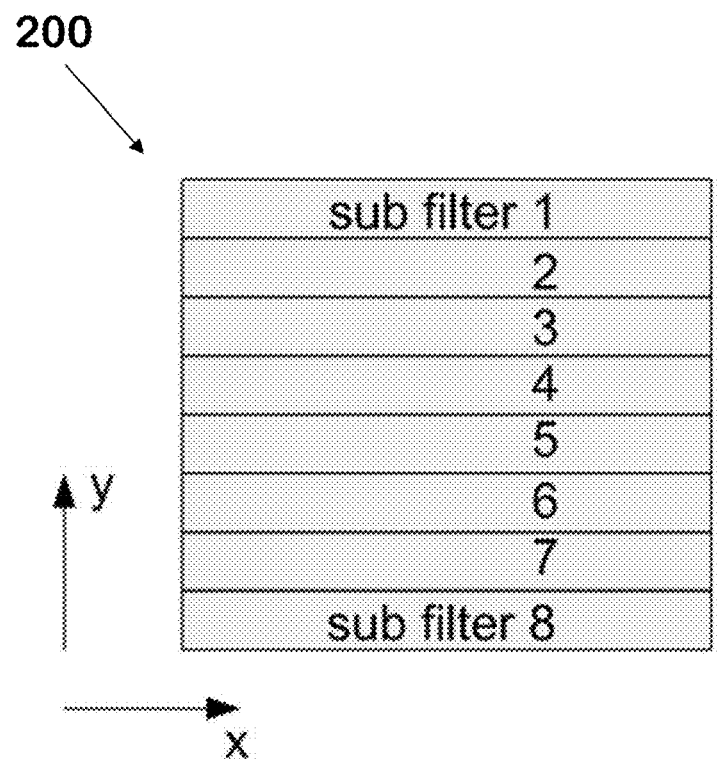
FIGS. 4A-4D present schematic illustrations of several embodiments of optical filters that comprise a plurality of sub-filters for use in the compact spectrometer system herein disclosed.
Figure 4B:
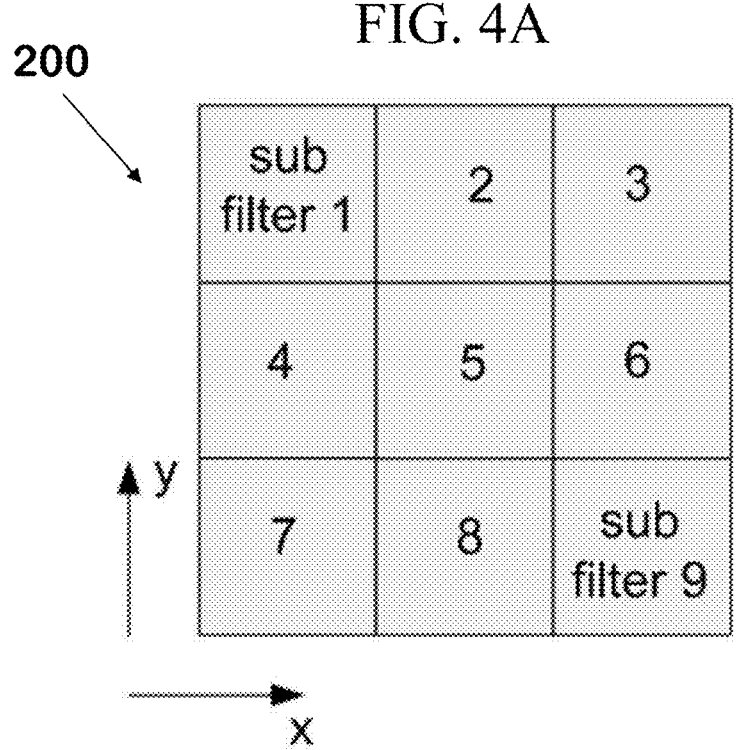

Reference is now made to FIGS. 4A and 4B, which show two non-limiting embodiments of an optical filter that comprises a plurality of sub-filters. FIG. 4A shows an optical filter in which the sub-filters (8 in the embodiment shown) are arranged along a single axis, while FIG. 4B shows an optical filter in which the sub-filters (9 in the embodiment shown) are tiled in two dimensions.

Depending on the number of sub-filters, the wavelength range accessible to the spectrometer can reach hundreds of nanometers. In the case of the use of a plurality of sub-filters, the approximate Fourier transforms formed at the image plane (i.e. one per sub-filter) overlap, and the signal obtained at any particular pixel of the detector will normally results from a mixture of the different Fourier transforms.

Figure 2C:
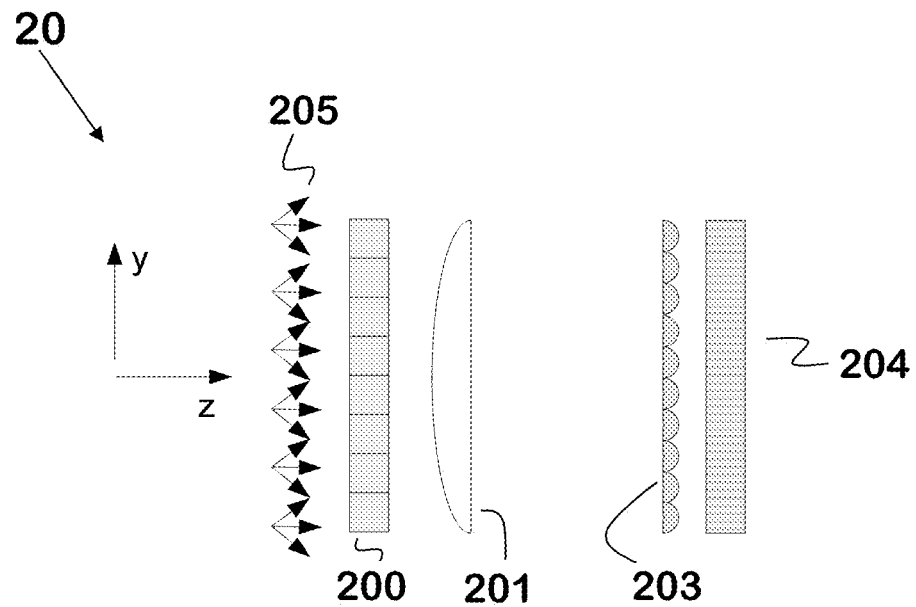

In order to separate the signals originating from different sub-filters, a micro-lens array is placed in a predetermined plane $P_2$ that is located between the first Fourier transform focusing element and the detector. Such micro-lens arrays are well-known in the art, e.g. in Plenoptic cameras. In preferred embodiments, the micro-lens array plane $P_2$ is substantially coincident with the focal plane of the first Fourier transform focusing element, and the detector plane $P_3$ is substantially coincident with the plane that includes the image of the optical filter created by the micro-lens array. Reference is now made to FIG. 2C, which shows schematically the optical layout of an embodiment of the compact spectrometer 20 that incorporates a micro-lens array 203 disposed such that it is in the focal plane of first Fourier transform focusing element 201 and such that detector 204 lies in the plane that includes the image of the optical filter created by the micro-lens array.

Figure 5:
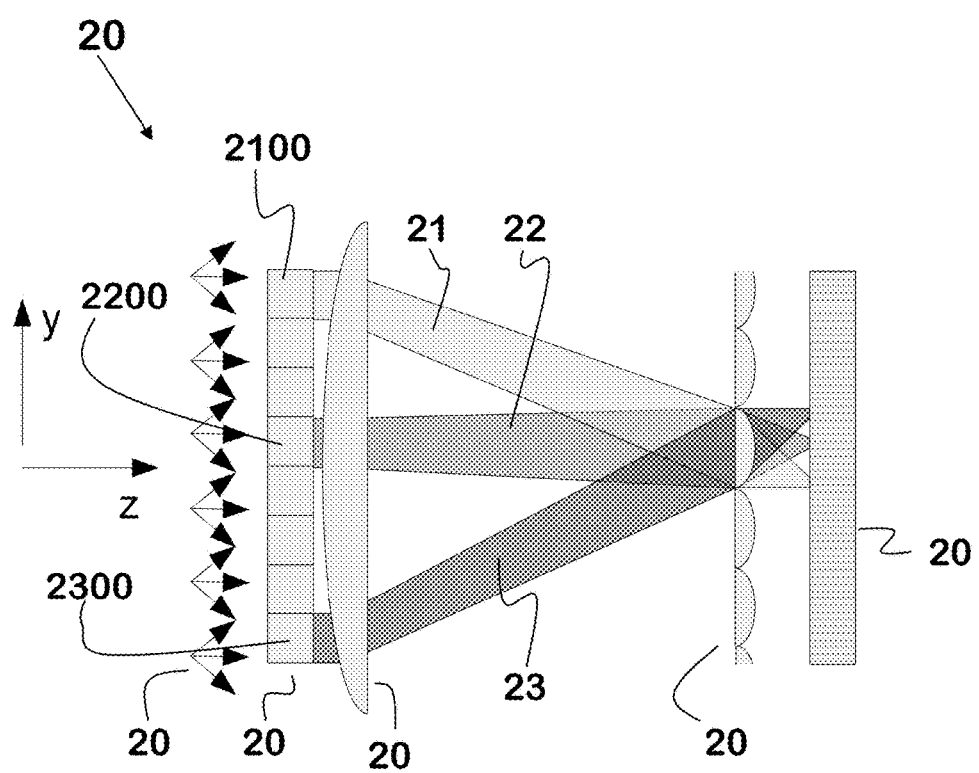
FIG. 5 presents a schematic illustration of the extraction of the Fourier images in a non-limiting embodiment of the invention herein disclosed.

In these embodiments, each micro-lens thus acts as a "super-pixel" that separates the light impinging upon it into components corresponding to the plurality of Fourier transformations produced by the plurality of sub-filters. Each micro-lens creates an image on the detector of the aperture of the optical filter. The "micro-image" thus formed represents the contribution to the signal from each part of the lens aperture (i.e. the optical filter) to the "super-pixel" covered by the micro-lens. Reference is now made to FIG. 5, which illustrates the decomposition of the signal by the micro-lens array into the separate Fourier transformed signals. Each micro-lens samples the overall Fourier image and each sample is then decomposed according to the signal origin at optical filter 200, enabling extraction of the Fourier image for each sub-filter.

In the particular embodiment illustrated in FIG. 5, optical filter 200 comprises a plurality of sub-filters aligned along a single axis. Light impinging on the Fourier transform focusing elements from three of the sub-filters (indicated in the figure as 2100, 2200, and 2300) leads to three different signals (210, 220, and 230, respectively) that are dispersed by the micro-lens array on the detector. The micro-lens array is disposed such that the light is dispersed on the detector along an axis parallel to the axis on which the sub-filters are aligned.

Figure 2D:
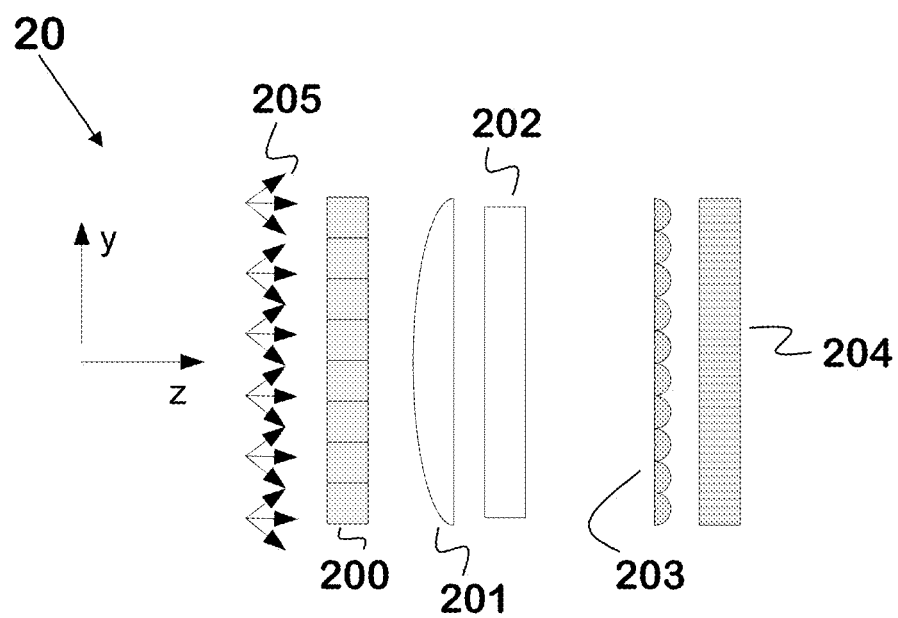

Reference is now made to FIG. 2D, which illustrates the optical layout of a preferred embodiment of compact spectrometer system 20 that includes a cylindrical micro-lens array. In these embodiments, a second Fourier transform focusing element 202 (in preferred embodiments, both of the Fourier transform focusing elements are plano-convex cylindrical lenses with the convex side facing the detector) is placed between the first Fourier transform focusing element and the micro-lens array. Second Fourier transform focusing element 202 is oriented such that its focal line is not aligned with that of the first Fourier transform focusing element. In preferred embodiments, the two focal lines are perpendicular. The second Fourier transform focusing element is placed such that the detector lies in its focal plane.

Table 1 provides a summary of the properties of the components of the compact spectrometer system in a typical embodiment. Note that in preferred embodiments, the f-numbers of the Fourier transform lenses and the micro-lenses are identical. The wavelength resolution of this embodiment is <10 cm$^{-1}$.

TABLE 1

| Parameter | Value | comments |
| --- | --- | --- |
| Length of sides of system aperture | 1 mm | aperture is equal to total filter size |
| sub-filter width | 0.125 mm | 8 sub-filters |
| First Fourier transform lens f-number | 4.2 | lens diameter 2 mm, focal length 6 mm |
| sensor pixel size | 5 µm | |
| micro-lens f-number | 4.2 | lens diameter 40 µm, focal length 169.7 µm; array pitch = diameter |
| Wavelength range per sub filter | 27.67 nm | |
| Overall wavelength range | 221.4 nm | = number of sub-filters × wavelength range of each sub-filter |

In some embodiments of the invention, an additional filter is placed in front of the compact spectrometer system in order to block light outside of the spectral range of interest (i.e. to prevent unwanted light from reaching the detector).

Figure 2E:
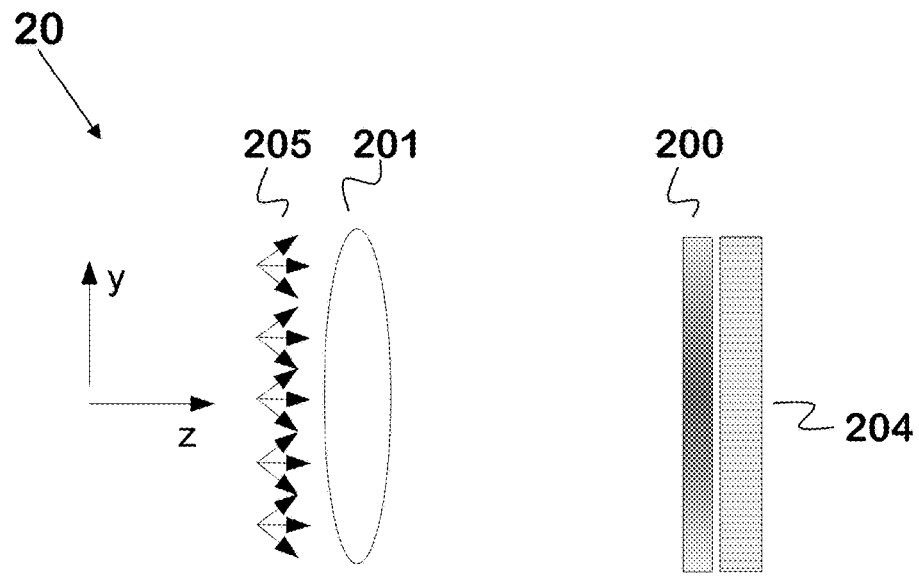

Reference is now made to FIG. 2E, which illustrates the optical layout of another embodiment of the invention herein disclosed. In this embodiment, optical filter 200 is located in close proximity to the detector, and first Fourier transform focusing element 201 is a radially symmetric biconvex, plano-convex, or aspheric lens; that is, a cylindrical lens is not used in this embodiment. Diffuse light 205 entering the spectrometer system is Fourier-transformed by first Fourier transform focusing element 201. Unlike the previously described embodiments, there is no angular wavelength encoding before the Fourier transform focusing element.

In this embodiment, the light that impinges upon the filter is directed in a wide range of angles, each spot on the detector corresponding to a different angle of incidence. As in the previous embodiments, the optical filter is designed such that its CWL depends on the angle of incidence. Thus, each concentric ring on the image will include only a narrow part of the spectrum of the light reaching the spectrometer system.

Figure 4C:
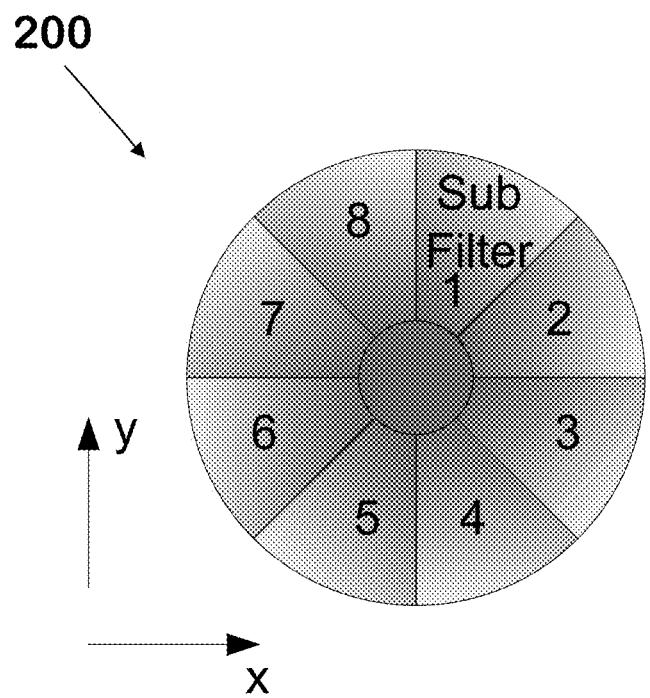
Figure 4D:
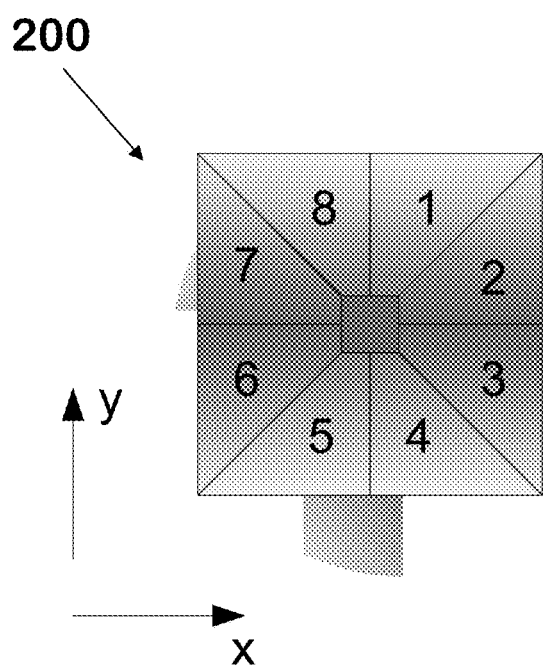

In embodiments in which the spectral range covered by a single optical filter is insufficient, as with the previous embodiments, an optical filter comprising a plurality of sub-filters with differing CWLs is used. Two non-limiting embodiments of the design of such optical filters are shown in FIGS. 4C and 4D. As the light reaching the detector in these embodiments is axially symmetric, the sub-filters are disposed about a center point. In the embodiments illustrated in FIGS. 4C and 4D, there is a gap in the center of filter 200. Since in general the variation of wavelength with angle of incidence is small at small incidence angles, not using the central part of the image is not expected to affect the quality of the spectrum significantly.

The embodiment illustrated in FIG. 2E involves a trade-off of added simplicity against reduced performance. The advantage of the embodiment illustrated in FIG. 2E is that the number of parts in the system can be reduced, since the optical filter can be fabricated on top of, or at least mounted on, the detector. On the other hand, each spot created on the image plane is composed of many optical rays (equivalent to many plane waves) whose incident angle is not identical. Specifically, each spot is composed of a ray bundle impinging on the detector over range of angles, where the center of this range is the angle created by the line connecting the center of the lens and the spot on the image and the line connecting the center of the lens and the center of the image. Depending on the f-number of first Fourier transform focusing element 201, this angle, which is inversely proportional to the f-number, can vary from a fraction of a degree to several degrees. Each ray in the ray bundle will experience a different filtering function, thus reducing the spectral resolution. For non-critical applications, the reduction in spectral resolution will be compensated for by the decreased complexity and cost of this embodiment of the system.

In some embodiments of the invention, the measurement of the sample is performed using scattered ambient light. In most cases, the scattered ambient light will not be sufficiently intense to provide a spectrum of sufficiently high quality. Therefore, in preferred embodiments of the invention, the compact spectrometer system incorporates a light source. The light source can be of any type (e.g. laser or light-emitting diode) known in the art appropriate for the spectral measurements to be made.

Because of its small size and low complexity, the compact spectrometer system herein disclosed can be integrated into a mobile communication device such as a cellular telephone. It can either be enclosed within the device itself, or mounted on the device and connected to it by any wired or wireless means for providing power and a data link known in the art. By incorporating the spectrometer system into a mobile device, the spectra obtained can be uploaded to a remote location, analysis performed there, and the user notified of the results of the analysis, as described in detail below. The spectrometer system can also be equipped with a GPS device so that the location of the sample being measured can be reported.

Because of its small size and low cost, the spectrometer system herein disclosed can also be integrated into kitchen appliances such as ovens (particularly microwave ovens), food processors, refrigerators etc. The user can then make a determination of the safety of the ingredients in real time during the course of food storage and preparation.

Figure 6A:
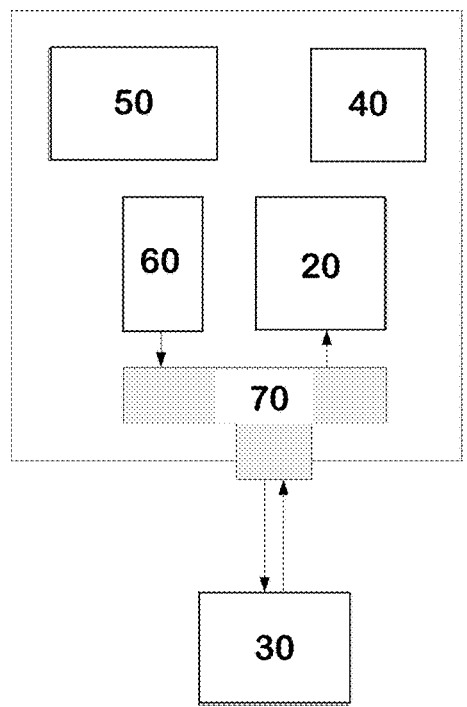
FIGS. 6A-6B present block diagrams of compact spectrometers incorporating the invention herein disclosed; and, FIG. 7 presents a block diagram of one embodiment of the connection of the invention herein disclosed to a communication network.
Figure 6B:
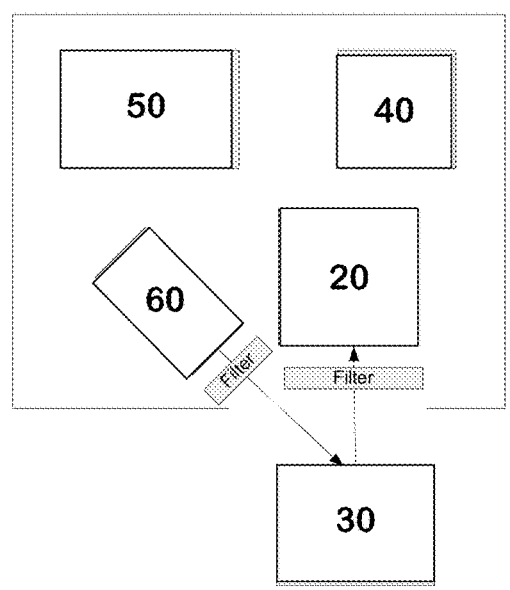

Reference is now made to FIG. 6, which illustrates two non-limiting embodiments of spectrometers for obtaining spectra of a sample 30 that incorporate the compact spectrometer system herein disclosed. The spectrometer incorporates, in addition to compact spectrometer system 20, a light source 60. In some embodiments, the light source may be a laser; in other embodiments, it may be a light-emitting diode (LED). The wavelength(s) and intensity of the light source will depend on the particular use to which the spectrometer will be put. The spectrometer also includes a power source (e.g. a battery or power supply) 40 and processing and control unit 50. In the embodiment shown in FIG. 6A, the spectrometer additionally incorporates I/O optics 70, while in the embodiment shown in FIG. 6B, in place of the I/O optics of the previous embodiment, optical filters are included, one between the light source and the sample, and the other between the sample and compact spectrometer system 20. One skilled in the art will recognize that the spectrometers herein disclosed can be adopted, with proper choice of light source, detector, and associated optics, for a use with a wide variety of spectroscopic techniques. Non-limiting examples include Raman, fluorescence, and IR or UV-VIS reflectance spectroscopies. Because, as described above, compact spectrometer system 20 can separate a Raman signal from a fluorescence signal, in some embodiments of the invention, the same spectrometer is used for both spectroscopies.

As mentioned above, a second problem for adapting spectroscopic techniques for determination of food safety is the complicated nature of the substance being tested and hence the complicated analysis that is necessary. In particular, if the intended user is an individual consumer, the use of the spectrometry system must be no more complicated than "point and shoot," and the analysis provided to the user without any extensive activity on his or her part.

In some embodiments of the invention, the spectrometer system comes equipped with a memory with a database of spectral data stored therein and a microprocessor with analysis software programmed in. The memory can be volatile in order that the user's own measurements can be incorporated into it. In other embodiments, the database and/or all or part of the analysis software is stored remotely, and the spectrometer system communicates with it via a network (e.g. a wireless network) by any appropriate method known in the art. In preferred embodiments in which the database is located remotely, it is continuously updatable. In this manner, each measurement made by a user of the spectrometer increases the quality and reliability of future measurements made by any user.

In a typical method of use of the compact spectrometer, the user illuminates the sample, a spectrum of which is to be obtained. The spectrum is then obtained as described above. The spectrum is then analyzed using any appropriate analysis method. Non-limiting examples of spectral analysis techniques that can be used include Principal Components Analysis, Partial Least Squares analysis, and the use of a neural network algorithm to determine the spectral components. The spectrum is thus analyzed to determine whether the spectrum of the complex mixture being investigated contains components consistent with the spectrum of a substance, mixture of substances, or microorganism, the presence of which is undesirable, and from the intensity of these components in the spectrum, whether their concentration is high enough to be of concern. Non-limiting examples of such substances include toxins, allergens, decomposition products, or harmful microorganisms. In preferred embodiments of the invention, if it is deemed likely that the sample is not fit for consumption, the user is provided with a warning.

In preferred embodiments of the invention, it is connected to a communication network that allows users to share the information obtained in a particular measurement. An updatable database located in the "cloud" (i.e. the distributed network) constantly receives the results of measurements made by individual users and updates itself in real time, thus enabling each successive measurement to be made with greater accuracy and confidence as well as expanding the number of substances for which a spectral signature is available.

Figure 7:
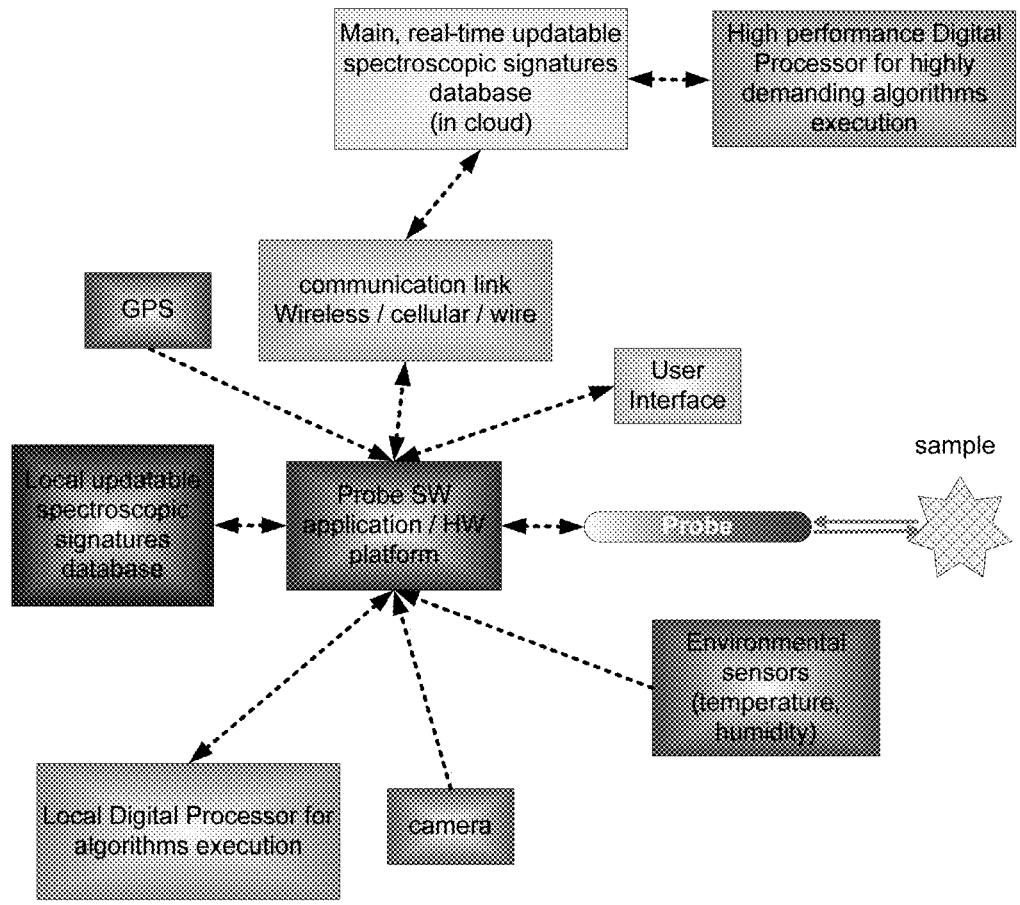

Reference is now made to FIG. 7, which presents a block diagram of the communication environment of the method disclosed herein for using the system disclosed herein. A probe, comprising a light source, compact spectrometer system 20 and associated optics has a logical connection to a platform comprising some or all of the hardware and software described above. The probe system may include additional components for providing information to the user. Non-limiting examples of such components include a GPS to link the food sampling with the location at which the sampling was performed; a camera for recording the visual impression of the sample; and sensors for measuring such environmental variables as temperature and humidity.

The block diagram shown in FIG. 7 also shows the logical links to the local or remote databases discussed above. In various embodiments of the invention, the conversion of the raw intensity data to a spectrum may be performed either locally (with a processor and software supplied with the spectrometer system) or remotely. Heavier calculations for more complicated analyses will in general be performed remotely.

In embodiments that incorporate remote data analysis, the data transferred to the remote system may include one or more of raw detector data; pre-processed detector data or post-processed detector data in which the processing was performed locally; or the spectrum derived from the raw detector data. These examples are not intended to be limiting, and are merely given to illustrate typical embodiments of the invention.

In some embodiments of the invention, the following signal processing scheme is used. First, an image or a series of images is captured by the image sensor in the spectrometer mentioned above. The images are analyzed by a local processing unit. This stage of analysis may include any or all of image averaging, compensation for aberrations of the optical unit, reduction of detector noise by use of a noise reduction algorithm, or conversion of the image into a raw spectrum. The raw spectrum is then transmitted to a remote processing unit; in preferred embodiments, the transmission is performed using wireless communication.

The raw spectrum is then analyzed remotely. First, noise reduction is performed. Then, in embodiments in which a Raman spectrum is being obtained, the Raman signal is separated from any fluorescence signal. Both Raman and fluorescence spectra are then compared to existing calibration spectra. After the calibration is performed, the spectra are analyzed using any appropriate algorithm for spectral decomposition; non-limiting examples of such algorithms include Principal Components Analysis, Partial Least-Squares analysis, and spectral analysis using a neural network algorithm. This analysis provides the information needed to characterize the sample that was tested using the spectrometer. The results of the analysis are then presented to the user.

What is claimed is:

1. A compact spectrometer system for obtaining a spectrum of a sample, the compact spectrometer system comprising:
    an optical detector configured to detect light emanating from the sample, wherein the optical detector is configured to measure spectral intensity and is configured to detect light of four or more wavelengths, and generate raw spectral data in response to the measured spectral intensity at the four or more wavelengths;
    a plurality of optical filters located between the sample and the optical detector, wherein the plurality of optical filters is configured to increase a spectral range of the spectrometer system from a first spectral range to a second spectral range, and wherein each optical filter of the plurality has a different central wavelength;

a local processing unit configured to convert the raw spectral data into processed spectral intensity data;

a communication module configured to be in communication with the local processing unit and a remote processing unit, wherein the communication module is configured to transmit the processed spectral intensity data from the local processing unit to the remote processing unit, and wherein the remote processing unit is configured to generate the spectrum of the sample in response to the processed spectral intensity data.

2. The compact spectrometer system according to claim 1, wherein the remote processing unit comprises a database of spectral information, the spectral information comprising one or more of raw detector data, pre-processed detector data, or post-processed detector data.

3. The compact spectrometer system according to claim 2, wherein the database is updated with sample spectral information generated from the measurement of the sample.

4. The compact spectrometer system according to claim 3, wherein the database is continuously updated in real time with sample spectral information generated from measurements made by one or more users of the compact spectrometer system.

5. The compact spectrometer system according to claim 3, wherein the database is accessible by a plurality of users of the compact spectrometer system, thereby allowing a user to share the sample spectral information generated from the measurement with one or more other users.

6. The compact spectrometer system according to claim 3, wherein the sample spectral information comprises one or more spectral signatures corresponding to one or more substances present in the sample, and wherein updating the database comprises expanding a number of substances for which a spectral signature is available.

7. The compact spectrometer system according to claim 2, wherein the spectral information in the database comprises spectra of a plurality of substances, and wherein the remote processing unit is configured to compare the spectrum of the sample with the spectra of the plurality of substances to determine presence of one or more of the plurality of substances in the sample.

8. The compact spectrometer system according to claim 7, wherein the remote processing unit is configured to perform spectral decomposition analysis of the spectrum of the sample to determine one or more sample spectral components, and wherein the remote processing unit is configured to compare the sample spectral components to one or more spectral components of the spectra of the plurality of substances to determine the presence of one or more of the plurality of substances in the sample.

9. The compact spectrometer system according to claim 1, wherein the remote processing unit is further configured to perform one or more of noise reduction of the processed spectral intensity data or calibration of the processed spectral intensity data using calibration data stored in the remote processing unit.

10. The compact spectrometer system according to claim 1, wherein the communication module is configured to transmit the processed spectral intensity data over a wireless communication network.

11. The compact spectrometer system according to claim 1, wherein the compact spectrometer system is enclosed within a mobile communication device comprising the communication module.

12. The compact spectrometer system according to claim 1, wherein the compact spectrometer system does not contain any dispersive optical elements.

13. The compact spectrometer system according to claim 1, wherein the optical detector comprises a two-dimensional detector array and wherein the plurality of optical filters comprise a filter array having a plurality of filter elements.

14. The compact spectrometer system according to claim 1, wherein the local processing unit is further configured to generate the spectrum of the sample in response to the raw spectral data.

15. The compact spectrometer system according to claim 1, further comprising a diffuser between the sample and the plurality of optical filters.

16. The compact spectrometer system according to claim 1, wherein the local processing unit is operably coupled to the optical detector.

17. The compact spectrometer system according to claim 1, wherein the local processing unit is configured to perform at least one of (a) averaging a plurality of independent measurements, (b) compensating for optical aberrations, or (c) reducing detector noise using a noise reduction process.

18. The compact spectrometer system according to claim 1, wherein the optical detector is configured to measure spectral intensity as a function of position.

* * * * *